United States Patent
Vik et al.

(10) Patent No.: US 10,140,004 B2
(45) Date of Patent: *Nov. 27, 2018

(54) DISPLAYING VISUAL ELEMENTS ON A MEDICAL DEVICE

(71) Applicant: CareFusion 303, Inc., San Diego, CA (US)

(72) Inventors: Daniel Vik, San Diego, CA (US); Sreelal Chandrasenan, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 436 days.

This patent is subject to a terminal disclaimer.

(21) Appl. No.: 14/939,875

(22) Filed: Nov. 12, 2015

(65) Prior Publication Data

US 2016/0110088 A1 Apr. 21, 2016

Related U.S. Application Data

(63) Continuation of application No. 12/987,472, filed on Jan. 10, 2011, now Pat. No. 9,190,010.

(51) Int. Cl.
| | |
|---|---|
| *G06F 3/0484* | (2013.01) |
| *G09G 5/00* | (2006.01) |
| *A61M 5/142* | (2006.01) |
| *G06F 19/00* | (2018.01) |
| *G16H 40/63* | (2018.01) |

(52) U.S. Cl.
CPC ......... *G06F 3/04847* (2013.01); *A61M 5/142* (2013.01); *G06F 19/00* (2013.01); *G06F 19/3468* (2013.01); *G09G 5/00* (2013.01); *G16H 40/63* (2018.01); *A61M 2205/505* (2013.01); *G09G 2320/066* (2013.01); *G09G 2320/0666* (2013.01); *G09G 2340/14* (2013.01); *G09G 2360/144* (2013.01); *G09G 2380/08* (2013.01)

(58) Field of Classification Search
CPC .. G06F 19/34; G06F 19/3406; G06F 19/3468; G06T 2210/41; G09G 2380/08
See application file for complete search history.

(56) References Cited

U.S. PATENT DOCUMENTS

| | | | |
|---|---|---|---|
| 9,190,010 B2 * | 11/2015 | Vik | ........................ G09G 5/00 |
| 2006/0026205 A1 | 2/2006 | Butterfield | |
| 2006/0229557 A1 | 10/2006 | Fathallah et al. | |
| 2007/0287931 A1 | 12/2007 | Dilorenzo | |
| 2008/0300572 A1 | 12/2008 | Rankers et al. | |
| 2009/0150865 A1 | 6/2009 | Young et al. | |

(Continued)

FOREIGN PATENT DOCUMENTS

WO WO-2008/059495 A2 5/2008

*Primary Examiner* — Antonio A Caschera
(74) *Attorney, Agent, or Firm* — Mintz Levin Cohn Ferris Glovsky and Popeo, P.C.

(57) ABSTRACT

A medical system includes a medical device and a display for displaying a plurality of visual elements. The plurality of visual elements are associated with functions of the medical device. The medical system also includes a plurality of visual profiles for facilitating in controlling visual appearance of the plurality of visual elements displayed on the display, and a visual profile selector for selecting at least one of the plurality of visual profiles based on a state of the medical device.

20 Claims, 3 Drawing Sheets

(56) References Cited

U.S. PATENT DOCUMENTS

2010/0100037 A1 4/2010 Cozmi et al.
2011/0022981 A1 1/2011 Mahajan et al.
2011/0047499 A1 2/2011 Mandro et al.

* cited by examiner

DISPLAYING VISUAL ELEMENTS ON A MEDICAL DEVICE

CROSS REFERENCE TO RELATED APPLICATION

The present application claims priority under 35 U.S.C. § 120 to U.S. patent application Ser. No. 12/987,472, filed Jan. 10, 2011, entitled DISPLAYING VISUAL ELEMENTS ON A MEDICAL DEVICE, the disclosure of which is incorporated herein by reference.

BACKGROUND

A display screen on a medical device allows for a clinician to visibly see some parameters of the medical device. However, adjustments of the display screen typically does not allow for optimal viewability. In particular, current medical devices do not allow for color customization to inform the user of how the medical device operates.

The drawings referred to in this description should be understood as not being drawn to scale except if specifically noted.

DESCRIPTION OF EMBODIMENTS

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, components, and circuits have not been described in detail as not to unnecessarily obscure aspects of the present embodiments.

The description below will first describe the components of medical system 100. The description will then describe the functionality of the components during use of medical system 100.

In general, medical system 100 allows for detailed configuration of the appearance of a display to ensure optimal viewability and display perception based on clinical practices and preferences. Moreover, adjustments are made based on environment. As a result, errors are reduced and care is improved.

In contrast, conventional systems have minimal configurability. For example, backlight and contrast level may be adjusted. However, the adjustments do not give optimal viewability for the light conditions. Moreover, the conventional systems don't allow for customization, such as color, to inform the user of how the device is configured to operate.

Figure 1:
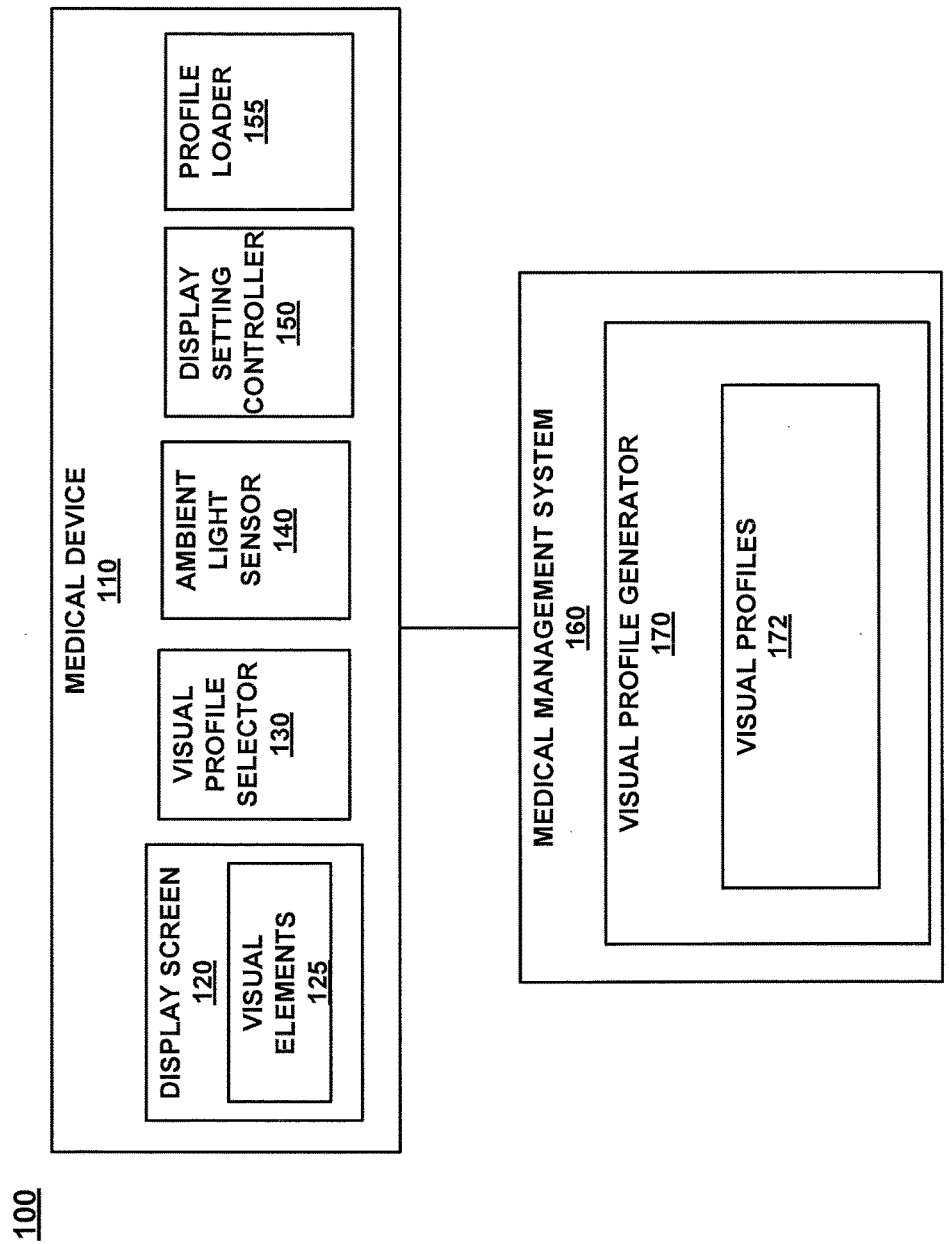
FIG. 1 illustrates an example of a medical system, in accordance with an embodiment of the present invention.

FIG. 1 depicts an embodiment of medical system 100. Medical system 100 includes medical device 110 and medical management system 160. In one embodiment, medical system 100 is a medication delivery system. In such an embodiment, medical device 110 is an infusion pump.

Medical management system 160 includes visual profile generator 170 and visual profiles 172. Visual profile generator 170 is for generating visual profiles 172. Visual profiles 172 are configured for facilitating in the control of the visual appearance of visual elements 125, which will be described in detail below.

Medical device 110 includes display screen 120, visual profile selector 130, ambient light sensor 140, display setting controller 150, and profile loader 155.

Display screen 120 is for displaying visual elements 125. Display screen 120 can be any display screen able to display visual elements 125. For example, display screen 120 is a color display screen for displaying visual elements 125.

Visual elements 125 are associated with functions of medical device 110. For example, visual elements 125 are associated with functions such, as but not limited to, parameters, medicine, or medicine dosage. Visual elements 125 can include icons, images, textures, fonts, etc., based on workflow, user inputs (e.g., user input fields), graphical libraries, etc.

Figure 2:
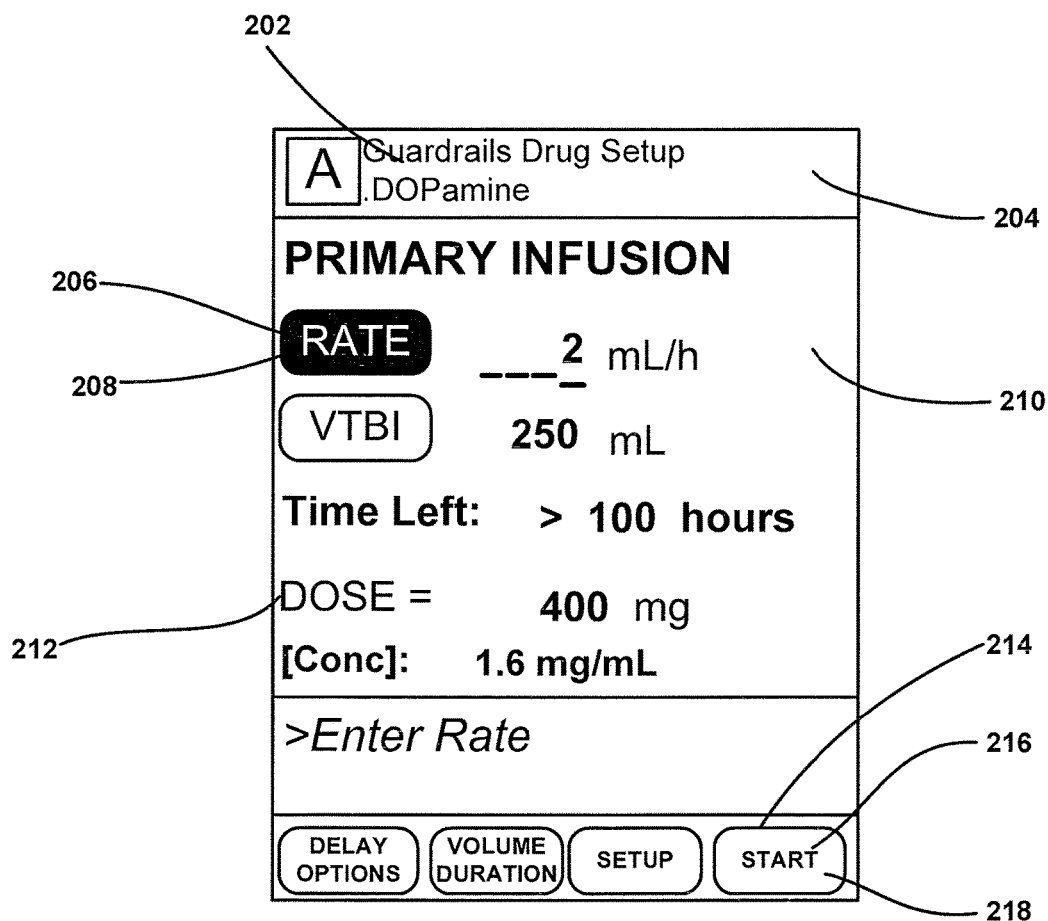
FIG. 2 illustrates an example of visual elements, in accordance with an embodiment of the present invention.

FIG. 2 depicts an embodiment of visual elements 125 displayed on display screen 120. In this embodiment, visual elements 125 include title bar text color 202, title bar color 204, selected button text color 206, selected button color 208, background color 210, text color 212, button border color 214, button text color 216 and button color 218. It should be appreciated that the number of elements and their definitions can vary depending on the graphical user interface engine (not shown) that is used to render visual elements 125 on display screen 120.

Visual profiles 172 facilitate in the control of the visual appearance of visual elements 125, as described above. In other words, visual profiles manage the visual configurations of visual elements 125 to enhance safe use of system 100. Also, the visual configuration of visual elements 125 enable power saving of medical device 110.

In general, visual profiles 172 allow for the customization of the visual performance of display screen 120. For example, visual profiles 172 allow for the visual customization (e.g., color customization) of visual elements 125. Visual profiles 172 depend on, among other things, criticality, classification, state of the device, state of the patient (e.g. heart rate), device association, state of the device class, clinical workflow, care area, clinical practices, environment (ambient light), device capabilities etc.

Visual profiles 172 include, but are not limited to, a color, a pattern, a bitmap, a texture or a theme.

In various embodiments, visual profiles 172 utilize a color space. For example, a RGB color space, CMYC color space or an HSV color space. Colors associated with visual profiles 172 can be a combination of a base color from a color space modified by adding contrast, brightness or saturation, by configuration or in conjunction with sensed ambient light, In one embodiment, visual profiles 172 include a color profile, which is a set of color configuration vectors that comprise each color region. The color regions are represented by a color configuration vector that specifies the perceived color of the region. The color profile, P is defined by the set:

$$P=\{C_{R1},C_{R2}\ldots C_{Rn}\}. \quad (1)$$

The configuration parameters for a particular color region to be display on display screen 120 is represented by a configuration vector, $$C_R=\{I_R,I_G,I_B,B_L\}, \quad (2)$$

where $I_R$, $I_G$, $I_B$ are the intensity of the red, green and blue color channels making the color, and $B_L$ is the intensity of the backlight. Although $B_L$ can be configured individually per color (in equation 2), limitations on backlight devices often require the $B_L$ parameter to be the same for all regions on the display screen at a given point in time, which is the case in this embodiment.

Accordingly, the color profile is, $$P=\{B_L,C'_{R1},C'_{R2}\ldots C'_{Rn}\}, \quad (3)$$

where $C'_R$ is the color vector $C_R$ without the individual configuration parameter $B_L$ present.

Visual profile selector 130 is for selecting visual profiles 172 based on a state of medical system 100 and/or medical device 110. States of medical system 100 and/or device 110 can be, but are not limited to, care area, power state, clinician, clinician preferences, patient, ambient light, alarm settings, infusing, priming, maintenance mode, pressure limits and pump orientation. In various embodiments, the states are dynamic.

For example, a first medical device is assigned to a male patient, and a second medical device is assigned to a female patient As such, visual profile selector 130 of the first medical device selects visual profiles 172 (e.g., a blue color) based on the first medical device assigned to the male patient. Likewise, visual profile selector 130 of the second medical device selects visual profiles 172 (e.g., a pink color) based on the second medical device assigned to the female patient.

In one embodiment, visual profile selector 130 utilizes a rule engine to select a visual profile. In such an embodiment, a rule may be stored in plain text or structured text, such as XML, which can be updated dynamically. For example, a rule can be, that if the current care area is "Neonatal," then use Profile 1, or if the current care area is "ICU, then use profile 2.

As a result, visual elements 125 of the first medical device for the male patient are customized with a blue color. Similarly, visual elements 125 of the second medical device are customized with a pink color, Moreover, visual profiles 172 based on the second medical device assigned to the female patient could also include a texture, such as parallel stripes. Accordingly, visual elements 125 of the second medical device are customized with a pink color with parallel stripes.

Additionally, visual profile selector 130 selects a visual profile of the visual profiles 172 based on the system state and applies the visual profile to an active profile. In one embodiment, visual profiles 172 are processed at run time to adjust to changes in ambient light.

In one embodiment, the aggregate state of medical device 110 is the sum of the state of medical device 110 and clinical configurations. It should be appreciated that an active profile can contain visual configurations from multiple visual profiles. In various embodiments, a visual profile includes visual configurations from multiple visual profiles. Also, sub-system states are prioritized to achieve the safest active profile based on inputs to medical device 110.

In various embodiments, visual profiles 172 includes rules. For example, if a patient's pulse rate is greater than X and care area is C, then visual profile 1 is selected. However, if the care area B, then visual profile 2 is selected. Accordingly, profile selector 130 utilizes rules based on the states, mentioned above, to select the appropriate visual profile.

Visual profiles 172 can be set by a pharmacy, hospital practices, biomed, clinician, and the like. In one embodiment, the pharmacy and hospital practices are a part of a drug library.

In one embodiment, visual profiles 172 are stored on memory (not shown) in medical management system 160. In another embodiment, visual profiles 172 are stored in memory (not shown) on medical device 110. For example, visual profiles 172 are a part of a firmware image or transferred from medical management system 160 through a data port and stored into memory of medical device 110. In another embodiment, visual profiles 172 may be accessed from a portable device (e.g., PDA, tablet, etc).

In various embodiments, visual profiles 172 are activated by applying the parameters in the profiles to different subsystems using a memory bus. The parameters are sent from memory to a graphical user interface engine which executes within a microprocessor. The interface engine applies the visual information (e.g., colors) to different visual elements 125 that are viewed on display 120 and then sends the updated screens to display 120.

Profile loader 150 is for managing a set of currently available visual profiles 172. For example, profile loader 150 coordinates uploading of new profiles from medical management system 160. Moreover, profile loader 150 allows modifications to visual profiles 172 made by a user locally on medical device 110.

Display setting controller 150 is for controlling the settings of display screen 120. For example, display setting controller 150 controls the display settings (e.g., backlight, contrast, etc.) in response to ambient light detected by ambient light sensor 140.

Figure 3:
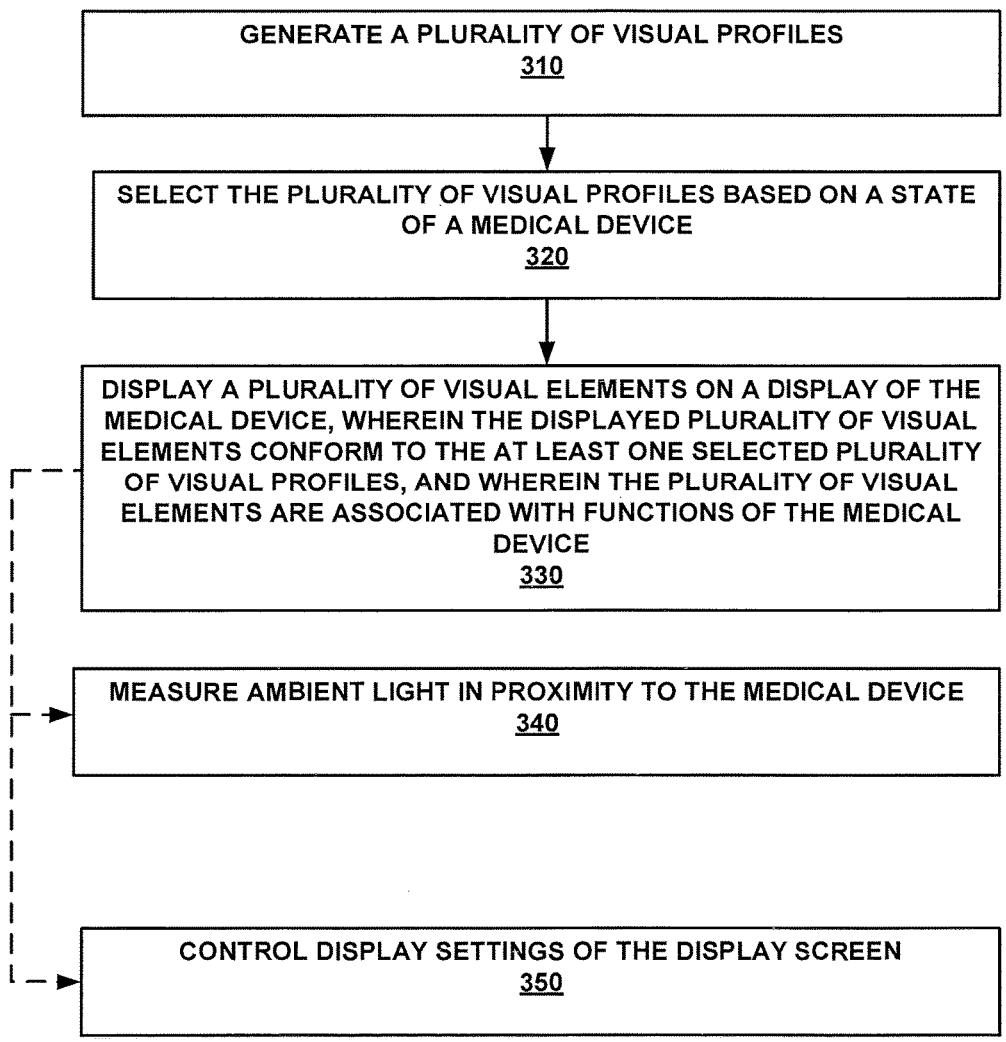
FIG. 3 illustrates a method for displaying visual elements, in accordance with an embodiment of the present invention.

FIG. 3 depicts an embodiment of a method 300 for displaying visual elements. In various embodiments, method 300 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 300 is performed at least by position medical system 100, as described in FIGS. 1 and 2.

At 310 of method 300, a plurality of visual profiles are generated. For example, visual profiles 172 are generated by visual profile generator 170.

At 320, the plurality of visual profiles are selected based on a state of a medical device. For example, a visual profile including a bitmap of animal is selected based on patient associated with medical device 110. Moreover, a visual profile including a red color is selected for when medical device 110 is infusing medication to the patient.

At 330, a plurality of visual elements are displayed on a display of the medical device, wherein the displayed plurality of visual elements conform to the at least one selected plurality of visual profiles, and wherein the plurality of visual elements are associated with functions of the medical device.

Continuing the example from above, displayed background color 210 is a bitmap of an animal because the background conforms to the visual profile that includes the bitmap of the animal. Similarly, text color 212 is red because the text color of the "dose" conforms to the visual profile that includes a red color for infusing medication to the patient.

In one embodiment, at 340, ambient light is measured in proximity to the medical device. For example, ambient light is measured by ambient light sensor 140.

In another embodiment, at 350, display settings of the display screen are controlled. For example, contrast and/or backlight is adjusted by display setting controller 150 based on the ambient light measured by ambient light sensor 140.

Various embodiments of the present invention are thus described. While the present invention has been described in particular embodiments, it should be appreciated that the present invention should not be construed as limited by such embodiments, but rather construed according to the following claims.

What is claimed is:

1. A medical system comprising:
   a medical device;
   a display for displaying a plurality of visual elements, wherein said plurality of visual elements are associated with functions of said medical device;
   a plurality of visual profiles for facilitating control of a visual appearance of said plurality of visual elements displayed on said display; and
   a visual profile selector for automatically selecting at least one of said plurality of visual profiles in accordance with one or more rules, said one or more rules based on one or more states of said medical device and providing for the automatic selection of said at least one visual profile when said one or more states are satisfied, said one or more states relating to at least one of an operating parameter associated with a treatment provided by said medical device and a care area associated with said medical device,
   wherein said visual profile selector selects a first visual profile from said plurality of visual profiles when said medical device is in a first state and selects a second visual profile from said plurality of visual profiles when said medical device is in a second state, and
   wherein said plurality of visual elements are selected from a group consisting of: text, a text color, a title bar, title bar text, a title bar background, a button border color, a button text color, a button color, a selected button text color, a selected button color, a work flow, one or more input fields, a graphical library, one or more textures, one or more background images, and one or more grayscale patterns.

2. The medical system of claim 1, wherein said medical device is an infusion pump.

3. The medical system of claim 1, wherein said plurality of visual elements further include one or more user inputs.

4. The medical system of claim 1, wherein said functions of said medical device are selected from a group consisting of: one or more parameters, medicine, and a dosage.

5. The medical system of claim 1, wherein said at least one of said plurality of visual profiles are selected from a group consisting of: a color, a pattern, a bitmap, a texture, and a theme.

6. The medical system of claim 1, wherein said plurality of visual profiles comprise:
   a set of color configuration vectors.

7. The medical system of claim 1, further comprising:
   an ambient light sensor.

8. The medical system of claim 1, wherein said state of said medical device is selected from a group consisting of: a power state, a clinician, a patient, and an amount of measured ambient light.

9. The medical system of claim 1, wherein said plurality of visual profiles are configured to be modified at said medical device.

10. A method for displaying visual elements, said method comprising:
    generating a plurality of visual profiles;
    automatically selecting at least one of said plurality of visual profiles in accordance with one or more rules, said one or more rules based on one or more states of a medical device and providing for the automatic selection of said at least one visual profile when said one or more states are satisfied, said one or more states relating to at least one of an operating parameter associated with a treatment provided by said medical device and a care area associated with said medical device; and
    displaying a plurality of visual elements on a display of said medical device,
    wherein said displayed plurality of visual elements conform to said at least one selected plurality of visual profiles,
    wherein said plurality of visual elements are associated with functions of said medical device,
    wherein said automatically selecting selects a first visual profile from said plurality of visual profiles when said medical device is in a first state and selects a second visual profile from said plurality of visual profiles when said medical device is in a second state, and
    wherein said plurality of visual elements are selected from a group consisting of: text, a text color, a title bar, title bar text, a title bar background, a button border color, a button text color, a button color, a selected button text color, a selected button color, a work flow, one or more input fields, a graphical library, one or more textures, one or more background images, and one or more grayscale patterns.

11. The method of claim 10, wherein said plurality of visual profiles are selected from a group consisting of: a color, a pattern, a bitmap, a texture, and a theme.

12. The method of claim 10, wherein said state of said medical device is selected from a group consisting of: a power state, a clinician, a patient, and an amount of measured ambient light.

13. The method of claim 10, wherein said automatically selecting said plurality of visual profiles based on said state of said medical device comprises:
    selecting said plurality of visual profiles based on a state of an infusion pump.

14. The method of claim 10, further comprising:
    measuring ambient light in proximity to said medical device.

15. The method of claim 10, further comprising:
    controlling a display setting of said display.

16. The method of claim 15, wherein said controlling said display setting comprises:
    controlling a contrast of said display.

17. The method of claim 15, wherein said controlling said display setting comprises:
    controlling a backlight of said display.

18. A non-transitory computer-readable medium containing instructions to configure at least one processor to perform operations comprising:

generating a plurality of visual profiles for facilitating control of a visual appearance of a plurality of visual elements displayed on a display of a medical device, said plurality of visual profiles comprising a set of color configuration vectors, each of said color configuration vectors comprising one or more color intensities and a backlight intensity for a region on said display of said medical device;

automatically selecting at least one of said plurality of visual profiles in accordance with one or more rules, said one or more rules based on one or more states of said medical device and providing for the automatic selection of said at least one visual profile when said one or more states are satisfied, said one or more states relating to at least one of an operating parameter associated with a treatment provided by said medical device and a care area associated with said medical device; and displaying said plurality of visual elements on said display of said medical device, wherein said displayed plurality of visual elements conform to said at least one selected plurality of visual profiles, and wherein said plurality of visual elements are associated with functions of said medical device, wherein said automatically selecting selects a first visual profile from said plurality of visual profiles when said medical device is in a first state and selects a second visual profile from said plurality of visual profiles when said medical device is in a second state, and wherein said plurality of visual elements are selected from a group consisting of: text, a text color, a title bar, title bar text, a title bar background, a button border color, a button text color, a button color, a selected button text color, a selected button color, a work flow, one or more input fields, a graphical library, one or more textures, one or more background images, and one or more grayscale patterns.

19. A medical system comprising:
a medical device;
a display for displaying a plurality of visual elements, wherein said plurality of visual elements are associated with functions of said medical device;
a plurality of visual profiles for facilitating control of a visual appearance of said plurality of visual elements displayed on said display; and
a visual profile selector for automatically selecting at least one of said plurality of visual profiles in accordance with one or more rules, said one or more rules based on one or more states of said medical device and providing for the automatic selection of said at least one visual profile when said one or more states are satisfied, said one or more states relating to at least one of an operating parameter associated with a treatment provided by said medical device and a care area associated with said medical device, wherein said visual profile selector selects a first visual profile from said plurality of visual profiles when said medical device is in a first state and selects a second visual profile from said plurality of visual profiles when said medical device is in a second state, and wherein said at least one of said plurality of visual profiles are selected from a group consisting of: a color, a pattern, a bitmap, a texture, and a theme.

20. A medical system comprising:
a medical device;
a display for displaying a plurality of visual elements, wherein said plurality of visual elements are associated with functions of said medical device;
a plurality of visual profiles for facilitating control of a visual appearance of said plurality of visual elements displayed on said display; and
a visual profile selector for automatically selecting at least one of said plurality of visual profiles in accordance with one or more rules, said one or more rules based on one or more states of said medical device and providing for the automatic selection of said at least one visual profile when said one or more states are satisfied, said one or more states relating to at least one of an operating parameter associated with a treatment provided by said medical device and a care area associated with said medical device, wherein said visual profile selector selects a first visual profile from said plurality of visual profiles when said medical device is in a first state and selects a second visual profile from said plurality of visual profiles when said medical device is in a second state, and wherein said one or more states of said medical device are selected from a group consisting of: a power state, a clinician, a patient, and an amount of measured ambient light.

* * * * *